Figure 1:
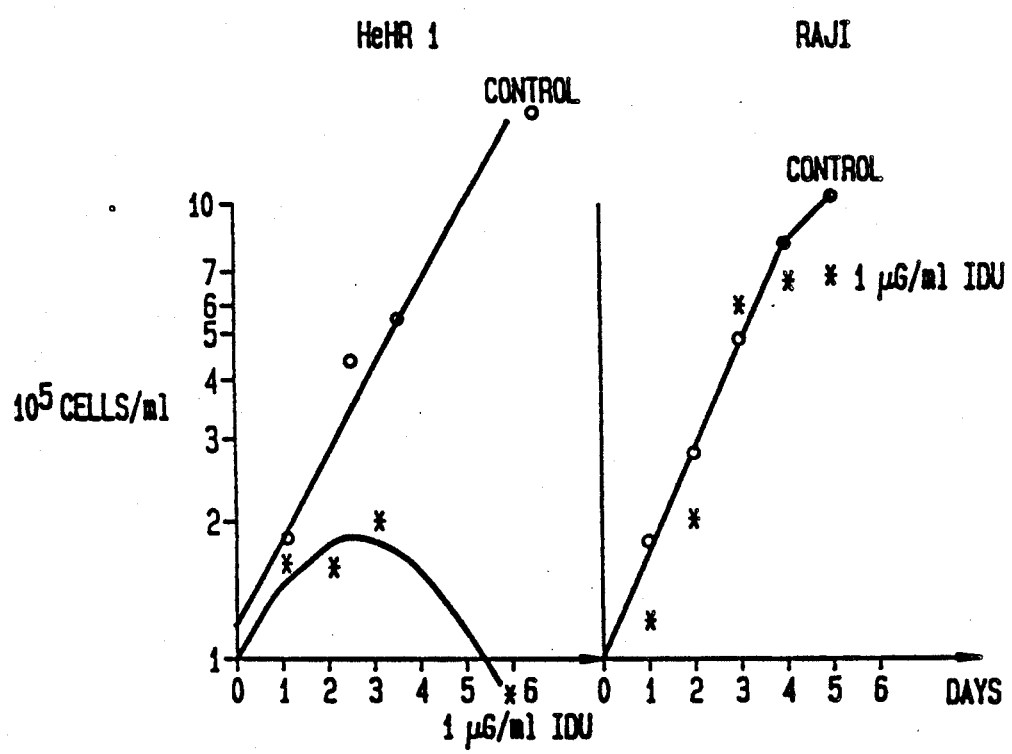

United States Patent [19]
Bergman et al.

[11] Patent Number: 4,990,510
[45] Date of Patent: Feb. 5, 1991

[54] SUBSTITUTED INDOLOQUINOXALINES

[75] Inventors: Jan O. E. Bergman, Spånga; Stig G. Åkerfeldt, Saltsjö-Duvnäs, both of Sweden

[73] Assignee: Leif Lundblad, Rhode St. Genese, Belgium

[21] Appl. No.: 102,147

[22] PCT Filed: Jan. 19, 1987

[86] PCT No.: PCT/SE87/00019
§ 371 Date: Nov. 18, 1987
§ 102(e) Date: Nov. 18, 1987

[87] PCT Pub. No.: WO87/04436
PCT Pub. Date: Jul. 30, 1987

[30] Foreign Application Priority Data
Jan. 21, 1986 [SE] Sweden ................................ 8600260

[51] Int. Cl.⁵ .................. C07D 487/04; A61K 31/495
[52] U.S. Cl. ..................................... 514/250; 544/343; 544/337
[58] Field of Search .................. 544/343, 337; 514/250

[56] References Cited

PUBLICATIONS

Morrison et al., Textbook, "Organic Chemistry", Allyn and Bacon, Inc., 1973, Bost., MA., U.S., p. 733.
15–Pharmacodynamics, vol. 66, 1967, 1282v Biological Characteristics of Phenazine Derivatives. II. Their Cytotoxic Effect on Cultured Cells, Katagiri et al. 1283c Biological Characteristics of Phenazine Derivatives. III. Antimycoplasma Effect, Ken Katagiri et al.
28–Heterocycles, vol. 84, 1976, 180166z Experiments on the Production of Antiviral and Antimicrobial Substances, 6, New 6–Substituted Endolo[2,3-b]quinoxalines, Knotz et al.
28–Heterocycles, vol. 104, 1986, 104:186375v Synthesis of Some New Indophenazinylpyrazoline and Isoxazoline Derivatives, Abdel Rahman et al.

Primary Examiner—John M. Ford
Attorney, Agent, or Firm—Browdy and Neimark

[57] ABSTRACT

Substituted indoloquinoxalines of the general formula I

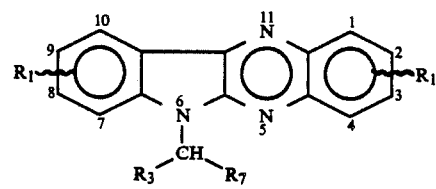

wherein
$R_1$ represents one of several, preferably 1 to 4, similar or different substituents in the positions 1–4 and/or 7–10, selected from halogen, prefrably Br, lower alkyl/alkoxy group having not more than 4 carbon atoms, trifluoromethyl group, trichloromethyl group;
X is a group —$(CH_2)_n$—$R_2$ wherein $R_2$ represents a nitrogen containing basic residue such as $NH_2$, $NHR_4$ or $NR_5R_6$ wherein $R_4$, $R_5$ and $R_6$ independently are lower alkyl or cykloalkyl and n is an integer of from 1 to 4 and
$R_3$ represents hydrogen, lower alkyl/cykloalkyl group having not more than 4 carbon atoms, and the physiologically acceptable addition products of the compounds with acids and halogen adducts, preferably adducts with iodine, iodine monochloride or iodine monobromide.

Also methods for preparing said compounds by reacting a compound of the formula II

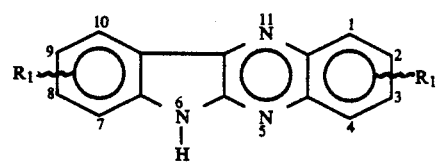

with a reactive compound containing the residue —$CHR_3R_7$ or by rearranging a compound the formula III

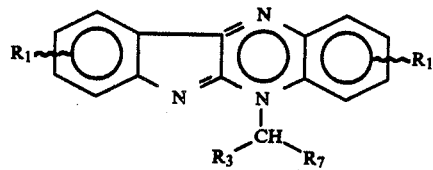

by heating are described.
The novel indoloquinoxalines have antiviral effect and have effect against cancer.

13 Claims, 5 Drawing Sheets

GROWTH OF TWO TYPES OF BURKITT LYMPHOMA CELLS IN THE PRESENCE OF IODODEOXYURIDINE (IDU)

COMPARISON BETWEEN THE TOXIC EFFECTS OF IDU AND B-196 ON BURKITT LYMPHOMA CELLS, HeHR-1-LINE

THE EFFECT OF B-196 ON THE GROWTH OF
BURKITT LYMPHOMA CELLS, RAJI-LINE

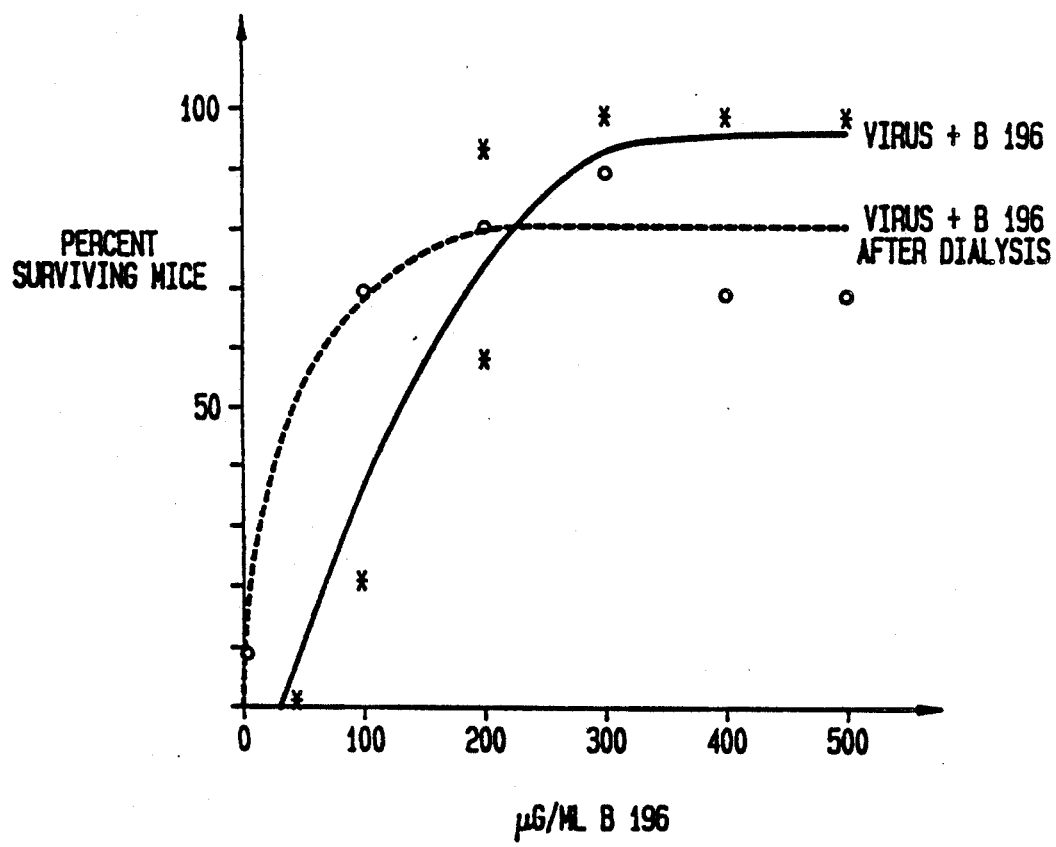

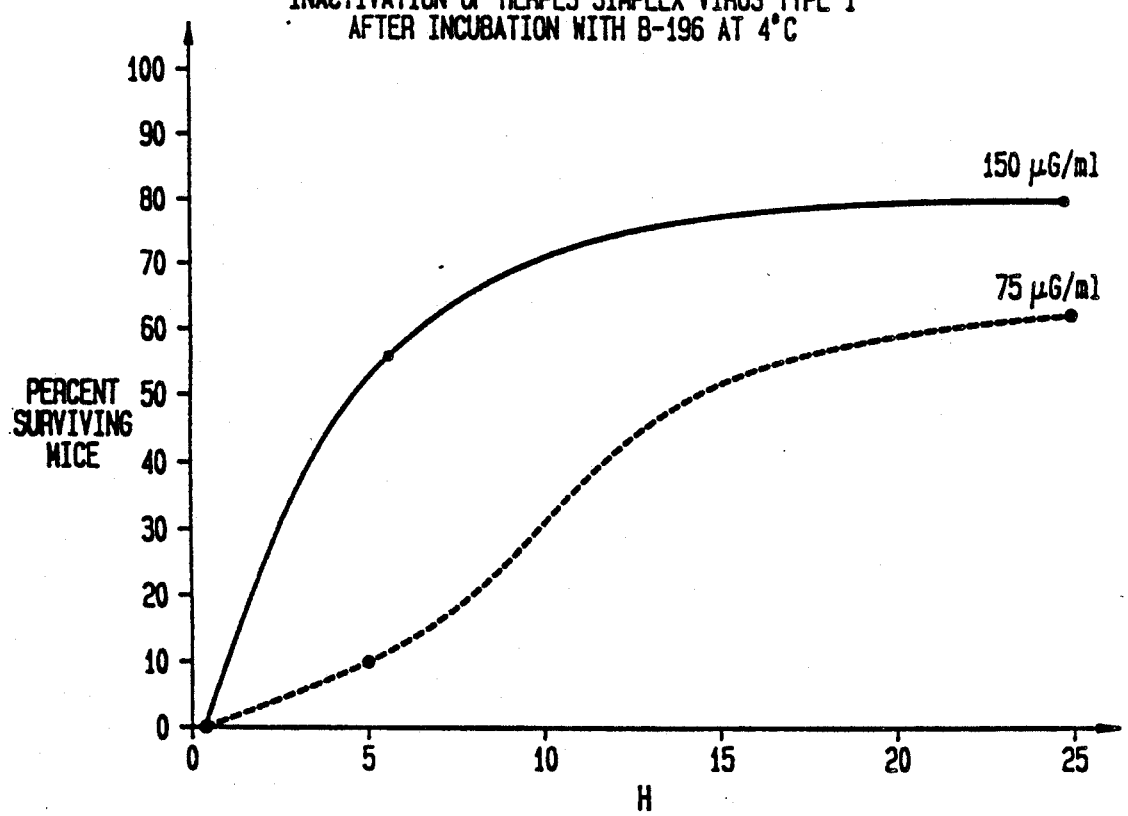

SUBSTITUTED INDOLOQUINOXALINES

The present invention relates to novel substituted indoloquinoxalines of the general formula I

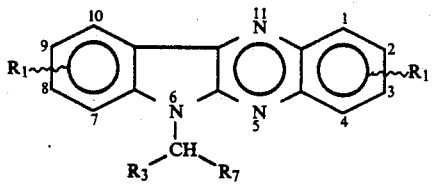

wherein $R_1$ represents one or several, preferably 1 to 4, similar or different substituents in the positions 1-4 and/or 7-10, selected from halogen, preferably Br, lower alkyl-/alkoxy group having not more than 4 carbon atoms, trifluoromethyl group, trichloromethyl group;

$R_7$ is a group —$(CH_2)_n$—$R_2$ wherein $R_2$ represents a nitrogen containing basic residue such as $N_2$, $NHR_4$ or $NR_5R_6$ wherein $R_4$, $R_5$ and $R_6$ independently are lower alkyl or cykloalkyl and n is an integer of from 1 to 4 and $R_3$ represents hydrogen, lower alkyl/cykloalkyl group having not more than 4 carbon atoms, and the physiologically acceptable addition products of the compounds with acids and halogen adducts, preferably adducts with iodine iodine monochloride or iodine monobromide.

The novel substituted indoloquinoxalines according to the present invention have a high antiviral effect and several of the compounds show a high anti-cancer effect.

A suitable group of compounds are compounds wherein X is —$(CH_2)_n$—$R_2$ wherein $R_2$ is —$N(CH_3)_2$ and n is 1.

The invention also relates to methods for preparing the novel indoloquinoxalines.

The compounds can be prepared by reaction of 6H-indolo-(2,3-b)-quinoxalines in 6-position with a reactive compound containing the residue —$CHR_3X$. Suitable solvents in this context are e.g. dimethylsulphoxide, dimethylformamide and dimethylacetamide. Alkylation in 6-position is favored by low temperature during the reaction. Minor amounts of 5-alkylated 5H-indolo(2,3-b)-quinoxalines are formed as byproduct in said alkylation. Previously ethanol has been used as solvent in this type of alkylation, F. Knotz, Sci. Pharm, 39, 20 (1970), F. Knotz, W. Wendelin, Sci. Pharm., 43, 249 (1975). This is unsuitable since with solvents of this type and at the stated temperature a relatively unfavorable isomer ratio is obtained. The 5-alkylated substances have an essentially lower activity.

The 5-alkylated products can like unalkylated starting material, if any, be removed by chromatography for instance on silica gel with a suitable eluent, for instance methylene chloride/methanol. The starting materials can be prepared by condensation of isatines with o-phenylene diamines. If unsymmetrical o-phenylene diamine is used for this, which is necessary for for instance preparation of 1-, 2-, 3- or 4-mono substituted starting materials, generally isomeric mixtures are obtained which can be difficult to separate. These difficulties can be avoided by preparing 6H-indolo(2,3-b)quinoxalines by condensation of oxindoles with 2-nitrosotoluidines as is shown below. R can be hydrogen or a nitrogen containing basic alkyl residue. With aminoalkyl groups as substituent

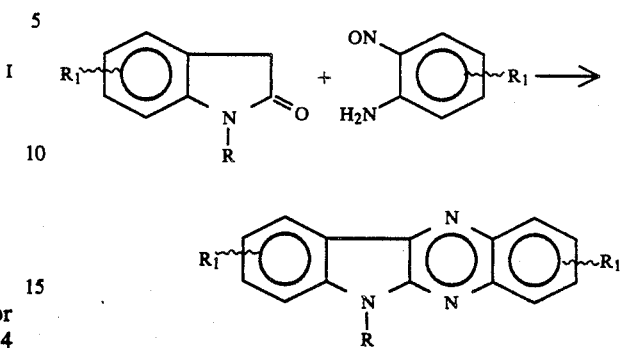

the active compounds can be prepared in one stage.

Another way to avoid the difficulties is to use N-alkylated o-phenylene diamines whereby 5-alkylated 5H-indolo(2,3-b)-quinoxalines are obtained. Then the substituent in 5-position can be removed by boiling with hydrogen bromide dissolved in acetic acid.

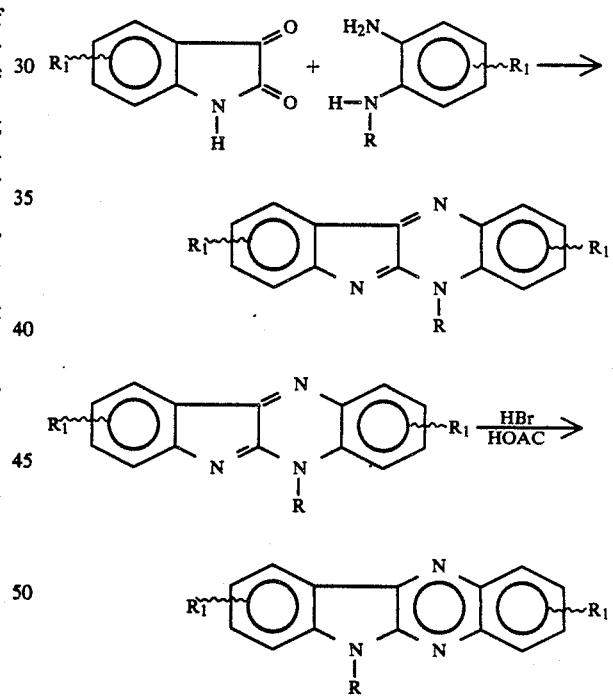

The 5-alkylated 5H-indolo(2,3-b)quinoxalines can be thermally rearranged to 6-alkylated 6H-indolo(2,3-b)quinoxalines. R can be an aminoalkyl group. Thus, by this rearrangement reaction there is an alternative preparation method for the active compounds.

The anions of indoloquinoxalines are easily alkylated by chloroacetonitrile whereby 6-cyanomethylindoloquinoxalines are obtained which by a suitable reduction can be converted to 6-(2-aminoethyl)indoloquinoxalines. Compounds of this type ban also be prepared as shown below.

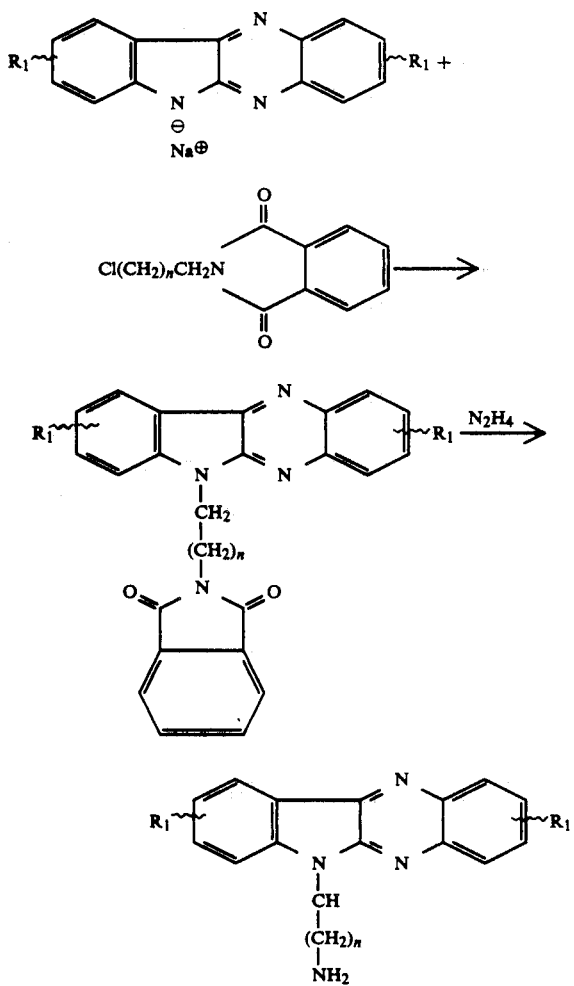

The bases easily can be converted to physiologically acceptable addition compounds such as hydrochloride, oxalate, tartrate and halogen adducts, preferably adducts with iodine, iodine monochloride or iodine monobromide.

A very interesting group of compounds according to the present invention are the adducts between phosphonoalkanoic acids, such as phosphonoformic acid, phosphonoacetic acid, phosphonopropionic acid, phosphonoglycolic acid and phosphonobutyric acid, and their 0-acetyl derivatives, and the indoloquinoxalines of formula I. The last mentioned adducts are interesting since the components per se are antiviral and intervene in different ways in the life cycles of DNA virus. Thus, it is known that phosphonoacetic acid and phosphonoformic acid are active against herpes virus,cf. Applied Microbiology, Volume 26, No. 3, September 1973, Shipkowitz et al, "Suppression of Herpes Simplex Virus Infection by Phosphonoacetic Acid", p. 264–267; Biochemistry, Volume 15, No. 2, 1976, S Leinbach et al, "Mechanism of Phosphonoacetate Inhibition of Herpesvirus-Induced DNA Polymerase", p. 426–430; Antiviral Research, I (1981), A Larsson and B Öberg, "Selective Inhibition of Herpesvirus DNA Synthesis by Foscarnet, p. 55–62; J.gen. Virol., 45, (1979), Bo Sundquist and Bo Öberg "Phosphonoformate Inhibits Reverse Transcriptase", p. 273–281.

Instead of using isolated adducts of the indoloquinoxalines with acids of course directly prepared mixtures of the indoloquinoxalines and the acids can be used.

The compounds according to the present invention have a high anti-cancer effect as can be seen from the following tests which show anti-tumor effects for the substituted indoloquinoxalines according to the present invention.

Indoloquinoxalines without a nitrogen containing basic residue in 6-position have been described in the literature, cf. Katagiri, K. et al., in Shionogi Kenkyosho Nempo 16 (1966) pp. 52–57. In said article a 6-acetylindoloquinoxaline is described. However, the indoloquinoxalines without any nitrogen containing basic residue in 6-position did not show any effect against virus and/or cancer and the shown inhibition of phages was insignificant.

Knotz (see above) has shown that indoloquinoxalines have effect against certain bacteria which effect however is clearly lower than the effect shown by preparations used today. Knotz has not reported any studies of the effects of the described indoloquinoxalines neither against virus nor against tumor. In view of this the effect shown by the compounds according to the present invention is very unexpected.

In the following tests two substituted indoloquinoxalines according to the present invention were used, viz.

B196=9-bromo-6(N,N-dimethylaminoethyl)-6H-indolo(2,3-b)-quinoxaline . HCl

B219=the 2,3-dimethylderivative of the above compound.

Test system with cancer cells

Burkitt lymphoma cells were obtained from professor Georg Klein, Karolinska Institutet. HeHrl-cells contain Epstein-Barr virus antigen on the surface of the cells while Raji cells contain the same antigen in the nucleus. The cells were grown in RPMI 1640 medium in the presence of 15% of fetal calf-serum, 2mM glutamine, 200 mg/1 penicillin and 200 mg/1 of streptomycine. L 1210 cells (mouse leukemia) were obtained from Dr. Miklos Degré, Rikshospitalet, Oslo. These cells were grown in RPMI 1640 medium with 10% horse serum.

Results

Figure 2:
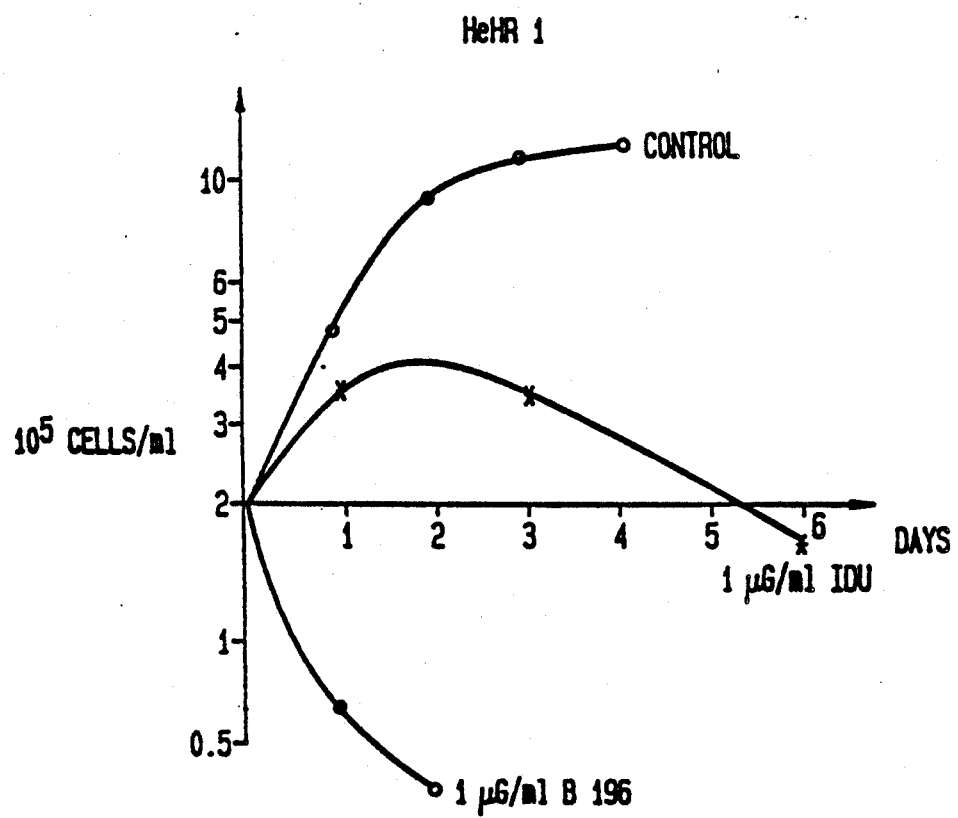
Figure 3:
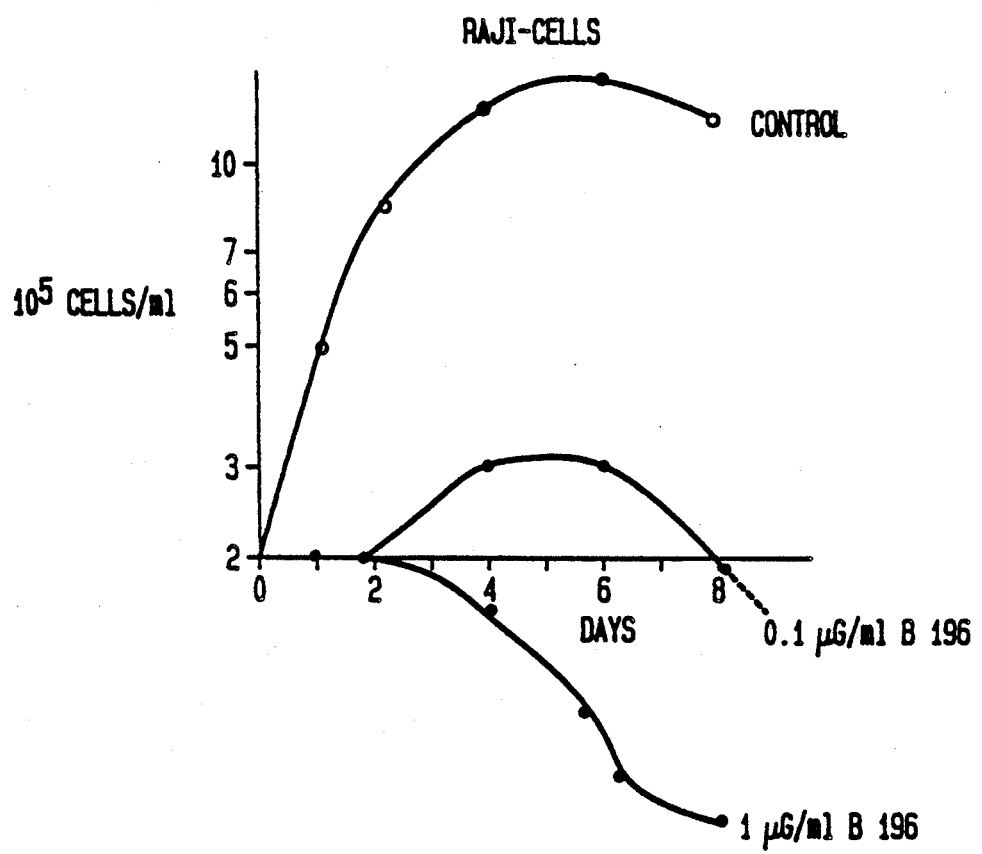

The results of the tests carried out are shown graphically in the enclosed FIGS. 1, 2 and 3, wherein FIG. 1 shows growth of 2 strains of Burkitt lymphoma cells in the presence of iododeoxyuridine (IDU) FIG. 2 shows the effect of B196 against HeHrl-cells FIG. 3 shows the effect of B196 against Raji-cells.

FIG. 1 shows that HeHrl-cells are sensitive to iododeoxy-uridine (well known anti-herpes compound), while Raji-cells are not. FIGS. 2 and 3 show that both these cell types are rapidly killed in the presence of indoloquinoxaline derivative (B196). Also osteogenic sarcoma cells and giant tumor cells (strain T4) were inhibited to 90% in their growth after 6 days test with 1 mg/l.

Experiments with mice have also been carried out. $LD_{50}$ intraperitoneally is of the order 1000 mg/kg and about 100 mg/kg intravenously. 20 mice were inocculated with 5 millions mouse ascites tumor cells intraperitoneally. 80 mg/kg of B219 were given daily for ten days. 2 mice died 22 days after treatment, 8 mice survived the whole test period (3 months). All controls were then dead. In two experiments with ascites lymphoma cells in mice a survival time of 50.9 days was obtained in the first experiment and 45.6 days in the second. The survival time for the controls, was 16.2 and 16.1 days respectively.

When testing at National Cancer Institute (USA) a statistically confirmed effect with mouse L1210 was obtained.

Substituted indoloquinoxalines according to the present invention also have a high antiviral effect. In tests carried out at National Cancer Institute a strong effect against HTLV-3-virus in tissue culture has been shown with concentration as low as 1 mg/l. As can be seen from the following tests the indoloquinoxalines also have a high antiviral effect against herpes simplex virus of both type 1 and 2.

Test methods against DNA virus

The virus strains were obtained from the National Bacteriological Laboratory, Stockholm. Herpes simplex type 1 and 2 were passaged intracerebrally in mice. For mouse experiments male mice 2-3 weeks old were used. Intracerebral infection was carried out by introducing the syringe 3 mm above the eye to a depth of approximately 3 mm. 0.03 ml virus suspension was injected above one eye and the substance above the other. Control groups obtained on one hand injection with physiological saline and on the other hand virus suspension.

Tissue culture experiments took place with human amnion AV3-cells. The cells were grown in glass-tubes (12×100 mm) in Eagles medium containing Earles salt solution and 10% of calf-serum. Tubes with a full-grown homogenous layer of cells were infected with virus (0.15 ml) and the virus was allowed to adsorb to cells for 1 hour at 37° C. The tubes were treated with substance dissolved in medium 24 hours and 0 hour before infection. Medium containing test-substance was changed every second day throughout the experiment. In each test a series of concentrations of the test-substance was investigated simultaneously so that about 50% reduction in cytopatogenic effect could be established ($ED_{50}$).

Results of the virus experiments

For all investigated synthetisized compounds $ED_{50}$ was between 0.5–2 mg/l in the tissue culture experiments.

The results of the virus experiments carried out are also shown graphically in the enclosed FIGS. 4 and 5 wherein FIG. 4 shows effect of dialysis on the antiviral properties of B196, FIG. 5 shows inactivation of HSV1-virus after incubation with two different concentrations of B196 vs. time.

In the experiments shown in FIG. 4 various concentrations of B-196 were mixed with herpes simplex virus type 1 and injected intracerebrally into mice immediately at or after dialysis, at 4° C. over night. No survivors were recorded in control groups.

FIG. 4 shows a dramatically improvement of the survival rate if virus was mixed with B196 before injection. The survival rate increases from 0 to 100%. Even if the virus-substance mixture is subjected to dialysis before injection the effect is almost equally pronounced. This probably indicates a direct interaction between the substance and the virus particle. (FIG. 4).

This belief is supported by experiments wherein virus and substance have been incubated together and injected in mice after different times.

In the experiments shown in FIG. 5 two concentrations of B-196 (75 and 150 μg/ml) were incubated for different times at 4° C. with herpes simplex virus type 1 and the infectivity of the mixtures were determined by intracerebral injection in mice Control virus was incubated at 4° C. for the same period of time. No survivors were registered in these groups.

FIG. 5 clearly shows that virus slowly is inactivated in the presence of the substance.

Some results with other compounds according to the invention are given in Table 1.

The invention is further illustrated by means of the following examples:

EXAMPLE 1

2,3-dimethyl-9-bromo-6H-indolo(2,3-b)quinoxaline

A mixture of 22.6 g 5-bromoisatin (0.1 mole), 15.0 g 4,5-dimethyl-o-phenylene diamine (0.11 mole) and 400 ml acetic acid is boiled under reflux for 4 hours. After cooling the product is sucked, washed with ethanol and dried. Yield 29 g, 89%. Recrystallisation from pyridine gives needle shaped crystals with melting point 319°–322° C.

In the corresponding manner also the following related intermediates are prepared

| $R_1$ substitution | mp °C. |
| --- | --- |
| 2-CH$_3$ | 297–300 |
| 2-OCH$_3$ | 324–327 |
| 3-OCH$_3$ | 284–287 |
| 3-COOH | 360 |
| 9-F | 302–304 |
| 9-Cl | 322–324 |
| 9-Br | 338–340 |
| 9-I | 354–356 |
| 2,3-di-CH$_3$ | 347–350 |
| 2-CH$_3$,9-Cl | 340–342 |
| 2-CH$_3$,9-Br | 347–350 |
| 9-CH$_3$ | 247–249 |
| 3,9-di-Cl | 328–330 |
| 7,9-di-Cl | 302–303 |
| 2,3-di-CH$_3$, 9-Cl | 331–334 |
| 2,3-di-Cl | 342–345 |
| 2,3,9-tri-Cl | 362–365 |
| 2,3,7,8-tetra-Cl | 402–404 |
| 2,3-diCl,7,8-diOCH$_3$ | 382–384 |

EXAMPLE 2

2-methyl-9-chloro-6H-indolo(2,3-b)quinoxaline

A solution of 1.68 g 5-chloroindol (0.01 mole) and 1.50 g 2-nitroso-N-methyl-p-toluidine (0.01 mole), 10 ml acetic acid is boiled under reflux for 1 hour. Finally hydrogen bromide is introduced and the mixture is boiled for further 2 hours. After cooling it is poured into water. The dried reaction product is recrystallized from acetic acid.

Yield 2.0 g 75%, mp 340°–343° C.

EXAMPLE 3

2-methyl-9-bromo-6H-indolo(2,3-b)quinoxaline

A solution of 2.26 g 5-bromoisatin (0.01 mole) and 1.36 g 2-amino N-methyl-p-toluidine (0.01 mole) in 15 ml acetic acid is boiled with reflux for 45 minutes. Finally hydrogen bromide is introduced and the mixture is boiled for further 2 hours. After cooling it is poured into water. The dried reaction product is recrystallized from acetic acid.

Yield 2.3 g, 74%, mp 347°–350° C.

EXAMPLE 4

9-methyl-6-(N,N-dimethylaminoethyl)-6H-indolo(2,3-b)quinoxaline 5.38 g sodium hydride (0.22 mole) is added to a solution of 15.9 g of N,N-dimethylamino-2-chloroethan-HCl (0.11 mole) in 400 ml dimethylformamide at 30° C. under nitrogen and well stirred. After about 5 minutes 23.3 g 9-methyl-6H-indolo-(2,3-b)quinoxaline (0.10 mole) is added in portions. The mixture is stirred at 30° C. until a clear solution is obtained After 24 hours at 30° C. the solvent is distilled off in vacuum at room temperature and the residue is purified by washing with water. The raw product is dried and dissolved in methyl acetate. When cooled down to −30° C. orange yellow crystals are obtained. Yield 21.1 g, 70%, mp 118°–120° C.

In the corresponding manner the following compounds are prepared
2,3-dimethyl-6-(N,N-dimethylaminoethyl)-6H-indolo(2,3-b)-quinoxaline, mp 138°–140° C.,
7,9-dichloro-6-(N,N-dimethylaminoethyl)-6H-indolo(2,3-b)-quinoxaline, mp 187°–189° C.

EXAMPLE 5

9-chloro-6-(N,N-dimethylaminoethyl)-6H-indolo(2,3-b)-quinoxaline-HCl 5.38 g sodium hydride (0.22 mole) are added to 600 ml dry dimethylsulphoxide, wherein 15.9 g N,N-dimethylamino-2-chloroethan-HCl (0.11 mole) has been dissolved at 30° C. under nitrogen and a good stirring. After about 5 minutes 5.4 g 9-dichloro-6H-indolo(2,3-b)quinoxaline (0.10 mole) are added. The mixture is stirred at 40° C. until a clear solution is obtained. Finally heating is carried out at 40° C. for 3 hours. The solvent is distilled off in vacuum at room temperature and the residue is dissolved in 2% boiling hydrochloric acid. When cooled the hydrochloride precipitates.

In the corresponding manner the hydrochloride of the following compounds belonging to the general formula are prepared Alternatively the raw dried base can be dissolved in acetone and the hydrochloride can be precipitated by introducing of hydrogen chloride.

| R₁ substituent | R₂ | R₃ | n | mp °C. |
| --- | --- | --- | --- | --- |
| 2,3-di-CH₃,9-Cl | N(CH₃)₂ | H | 1 | 235–240 |
| 2,3-di-CH₃,9-Br | N(CH₃)₂ | H | 1 | 225–228 |
| 2-CH₃,9-I | N(CH₃)₂ | H | 1 | 237–240 |
| 3,9-di-Cl | N(CH₃)₂ | H | 1 | 254–257 |
| 9-Cl | N(CH₃)₂ | H | 1 | 221–223 |
| 7,9-di-Cl | N(CH₃)₂ | H | 1 | 254–257 |

EXAMPLE 6

2,3-dimethyl-9-bromo-6-(N,N-dimethylaminoethyl)-6H-indolo-(2,3-b)quinoxaline

To a suspension of 5.38 g sodium hydride (0.22 mole) in 600 ml dry dimethylsulphoxide maintained at 35° C. 32.6 g 2,3-dimethyl-9-bromo-6H-indolo(2,3-b)quinoxaline (0.10 mol) is added under nitrogen and with good stirring. 30 minutes after completed addition 15.9 g N,N-dimethylamino-2-chloroethane-HCl (0.11 mole) are added at 35° C. The mixture is stirred at 35° C. for four hours and then the solvent is distilled off in vacuum at room temperature. The residue is dissolved after soaking out with water in methylacetate and slowly cooled to −30° C. whereby the base crystallizes out. Yield 22 g, 55%, mp. 146°–147° C.

In the corresponding manner the following compounds are prepared:
2,3-dimethyl-9-bromo-6-(N,N-diisopropylaminoethyl)-6H-indolo
(2,3-b)quinoxaline, mp. 121°–123° C.
9-fluoro-6-(N,N-dimetylaminoethyl)-6H-indolo(2,3-b)quinoxaline, mp. 101°–102° C.
2,3-dimethyl-9-bromo-6-(morpholinoethyl)-6H-indolo(2,3-b)quinoxaline, mp. 208°–210° C.

EXAMPLE 7

7,9-dichloro-6-(N,N-dimethylaminoethyl)-6H-indolo(2,3-b). quinoxaline-HCl 2.64 g sodium hydride (0.11 mole) are added to 300 ml dry dimethylsulphoxide wherein 7.95 g N,N-dimethylamino-2-chloroethane HCl (0.055 mole) have been dissolved at 30° C. under nitrogen and with good stirring. After about 5 minutes 14.4 g 7,9-dichloro-6H-indolo-(2,3-b)quinoxaline (0.05 mole) is added. The mixture is stirred at 50° C. until a clear solution is obtained. Finally heating is carried out at 60° C. for 3 hours. The solvent is distilled off in vacuum at room temperature and the residue is dissolved in methanol after soaking out with water. The mixture of the raw base then is subjected to chromatography on silica gel with methanol as eluent, the following being obtained in the order stated; a slight amount of non-reacted 7,9-dichloro-6H-indolo(2,3-b)quinoxaline, 7,9-dichloro-6-(N,N-dimethylaminoethyl)-6H-indolo(2,3-b)quinoxaline and finally 7,9-dichloro-5-(N,N-dimethylaminoethyl)-5H-indolo(2,3-b)quinoxaline (22%). The dried 6-substituted base is dissolved in acetone and the hydrochloride is precipitated by introducing hydrogen chloride Yield 7 g, 39%, mp 254°–257° C.

EXAMPLE 8

9-methyl-6-(N,N-dimethylaminoethyl-6H-indolo(2,3-b)-quinoxaline-HCl 5.06 g sodium (0.22 mole) is dissolved in 550 ml dry ethanol, 15.9 g N,N-dimethylamino-2-chloroethane-HCl (0.11 mole) is added followed by 23.3 g 9-methyl-6H-indolo(2,3-b)quinoxaline (0.10 mole). The mixture is boiled for 4 hours, cooled and filtered. The filtrate finally is concentrated in 2% warm hydrochloric acid. The hydrochloride is obtained as yellow crystals with slowly cooling. Yield 21 g, 62%, mp. 240°–242° C.

EXAMPLE 9

9-chloro-6-(N,N-dimethylaminoethyl)-6H-indolo(2,3-b)-quinoxaline-HCl 5.06 g sodium (0.22 mole) is dissolved in 300 ml 2-methoxyethanol, 15.9 g N,N-dimethylamino-2-chloroethane-HCl (0.11 mole) is added followed by 25.4 g 9-chloro-6H-indolo(2,3-b)quinoxaline (0.10 mole). The mixture is heated for 3 hours at 100° C., cooled and filtered. The filtrate is concentrated and poured into water. The raw base obtained is filtered off and washed with water and subjected to chromatography on silica gel with methanol as eluent. The purified base is dissolved after drying in acetone. The hydrochloride is precipitated by slowly dropwise adding concentrated hydrochloric acid with stirring. Yield 23.2 g, 66%, mp. 243°–246° C.

EXAMPLE 10

9-methyl-6-(N,N-dimethylaminoethyl)-6H-indolo(2,3-b)-quinoxaline-ICl 3.04 g 9-methyl-6-(N,N-dimethylaminoethyl)-6H-indolo(2,3-b)quinoxaline (0.01 mole) is dissolved in 50 ml methanol. 1.62 g iodine chloride (0.01 mole) is added and the mixture is boiled 5 minutes. After cooling the crystals formed are sucked, 4.1 g; 87%, mp. 101°–103° C.

In the corresponding manner the following compound is prepared: 2,3-dimethyl-6(N,N-dimethylaminoethyl)6H-indolo(2,3-b)-quinoxaline-ICl, mp. 183°–185° C.

EXAMPLE 11

9-methyl-5-(N,N-dimethylaminoethyl)-5H-indolo(2,3-b)quinoxaline 1.79 g (N,N-dimethylaminoethyl)-o-phenylenediamine (0.01 mole) and 1.61 g 5-methyl isatin (0.01 mole) are boiled 30 minutes in 25 ml acetic acid. The reaction solution is concentrated under reduced pressure and then is made alkaline with 5% sodium hydroxide solution. The precipitated base is washed, dried and recrystallised from methanol/water. Yield 2.2 g; 76%, mp. 150°–152° C.

In the corresponding manner the following compounds are prepared:
9-bromo-5-(N,N-dimethylaminoethyl)-5H-indolo(2,3-b)quinoxaline, mp. 152°–154° C.
7,9-dichloro-5-(N,N-dimethylaminoethyl)-5H-indolo(2,3-b)quinoxaline, mp. 180°–182° C.

EXAMPLE 12

9-methyl-6-(N,N-dimethylaminoethyl)-6H-indolo(2,3-b)quinoxaline 3.04 g 9-methyl-5-(N,N-dimethylaminoethyl)-5H-indolo(2,3-b)quinoxaline (0.01 mole) is heated to 250° C. for 2 hours. The reaction mixture is dissolved in methanol and subjected to chromatography on silica gel with methanol as eluent whereby the following components are obtained in the order stated:
9-methylindolo(2,3-b)quinoxaline and
9-methyl-6-(N,N-dimethylaminoethyl)-6H-indolo(2,3-b)quinoxalinea nd finally a slight amount of non-reacted starting material.
Yield 6-substituted compound 1.1 g; 36%, mp. 118°–120° C.

In the corresponding manner the following compounds are prepared:
2,3-dimethyl-6-(N,N-dimethylaminoethyl)-6H-indolo(2,3-b)-quinoxaline, mp. 138°–240° C.
7,9-dichloro-6-(N,N-dimethylaminoethyl)-6H-indolo(2,3-b)-quinoxaline, mp. 187°–189° C.

Typical compounds according to the invention

| R1 | R2 | R3 | n | smp °C. |
|---|---|---|---|---|
| 2-OCH3 | N(CH3)2 | H | 1 | 224–227 (HCl) |
| 3-CH3 | N(CH3)2 | H | 1 | 248–250 (HCl) |
| 3-NO2 | N(CH3)2 | H | 1 | 292–295 (HCl) |
| 3-COOH | N(CH3)2 | H | 1 | 302–305 (HCl) |
| 3-OCH3 | N(CH3)2 | H | 1 | 228–230 (HCl) |
| 9-CH3 | N(CH3)2 | H | 1 | 118–120 (base) |
| 9-CH3 | N(CH3)2 | H | 1 | 251–253 (HCl) |
| 9-OCH3 | N(CH3)2 | H | 1 | 231–234 (HCl) |
| 9-F | N(CH3)2 | H | 1 | 101–102 (base) |
| 9-F | N(CH3)2 | H | 1 | 238–240 (HCl) |
| 9-Cl | N(CH3)2 | H | 1 | 232–255 (HCl) |
| 9-Cl | N[CH(CH3)2]2 | H | 1 | 290–295 (HCl) |
| 9-Br | N(CH3)2 | H | 1 | 260–262 (HCl) |
| 9-Br | N(CH3)2 | H | 1 | 224–227 (oxalate) |
| 9-Br | N(CH3)2 | H | 1 | 207–211 (ICl) |
| 9-Br | N(CH3)2 | H | 1 | 254–257 (HCl) |
| 9-I | N(CH3)2 | H | 1 | 280–285 (oxalate) |
| 9-I | N(CH3)2 | H | 1 | 204–208 (ICl) |
| 2,3-di-CH3 | N(CH3)2 | H | 2 | 146–147 (base) |
| 2,3-di-CH3 | N(CH3)2 | H | 1 | 138–140 (base) |
| 2,3-di-CH3 | N(CH3)2 | H | 1 | 234–236 (HCl) |
| 2,3-di-CH3 | N(CH3)2 | H | 1 | 219–221 (oxalate) |
| 2,3-di-CH3 | N(CH3)2 | H | 1 | 183–185 (ICl) |
| 2,3-di-CH3 | 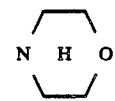 (morpholino) | H | 1 | 183–185 (base) |
| 3,9-di-Cl | N(CH3)2 | H | 1 | 254–257 (HCl) |
| 7,9-di-Cl | N(CH3)2 | H | 1 | 187–189 (base) |
| 7,9-di-Cl | N(CH3)2 | H | 1 | 254–257 (HCl) |
| 2-CH3,9-Cl | N(CH3)2 | H | 1 | 123–125 (base) |
| 2-CH3,9-Cl | N(CH3)2 | H | 1 | 230–233 (HCl) |
| 2-CH3,9-Br | N(CH3)2 | H | 1 | 279–282 (oxalate) |
| 2-CH3,9-Br | N(CH3)2 | H | 1 | 217–220 (HCl) |
| 3-Cl,9-Br | N(CH3)2 | H | 1 | 291–295 (oxalate) |
| 2,3-di-CH3,9-Cl | N(CH3)2 | H | 1 | 252–255 (HCl) |
| 2,3-di-CH3,9-Br |  (morpholino) | H | 1 | 208–210 (base) |
| 2,3-di-CH3,9-Br | N(CH3)2 | H | 1 | 225–228 (HCl) |
| 2,3-di-CH3,9-Br | N[CH(CH3)2]2 | H | 1 | 216–219 (HCl) |
| 2,3,7,8-tetra-Cl | N(CH3)2 | H | 1 | 282–284 (HCl) |
| 2,3-diCl-7,8-diMeO | N(CH3)2 | H | 1 | 280–282 (HCl) |
| 2,3-diCH3,7-Br | N(CH3)2 | H | 3 | 216–218 (HCl) |
| 2,3-diCH3,7-Br | N(CH3)2 | H | 4 | 212–214 (HCl) |

EXAMPLE 13

6-cyanomethyl-6H-indolo(2,3-b)quinoxaline

Indoloquinoline (10.95 g) is dissolved in dry dimethylsulfoxide (1.0 ml) under nitrogen and sodium hydride (1.3 g) is added with good stirring at 35C. After completed hydrogen gas generation (about 30 minutes) chloroacetonitrile (4.0 g) was dropped in with stirring at 20° C. After I day at this temperature water (20 ml) is added and crystals formed of pure 6-cyanomethyl indoloquinoxaline (8.9 g) are sucked and washed with methanol followed by water. The mother liquor is poured into a large amount of water and the precipitate formed is dried and purified by chromatography on silica gel with methylene chloride/methanol as eluent. In this manner further 3.0 g of 6-cyanomethyl-6H-indolo(2,3-b) quinoxaline is obtained. Thus, the total yield is 11.9 g, 92%, mp. 231°–232° C.

In the corresponding manner the following compounds are prepared
2,3-dichloro-6-cyanomethyl-6H-indolo(2,3)quinoxaline, mp. 258°–260° C.
2,3-dimethyl-6-cyanomethyl-6H-indolo(2,3-b)quinoxaline, mp. 244°–246° C.
2,3,9-trichloro-6-cyanomethyl-6H-indolo(2,3-b)quinoxaline, mp. 296°–298° C.
2,3-dimethyl-9-chloro-6-cyanomethyl-6H-indolo(2,3-b)quinoxaline, mp. 286°–288° C.

EXAMPLE 14

6-(2-aminoethyl)-6H-indolo(2,3-b)quinoxaline . HCl 6-cyanomethyl-6H-indolo(2,3-b)quinoxaline (2.58 g) is heated with reflux with lithium aluminum hydride (0.60 g) in tetrahydrofuran (40 ml) for 6 hours, and then water (2 ml) is dropped thereto cautiously. After stirring for 1 hour solid material is removed by separation and the rest is concentrated. The rest is dissolved in dry ether and the base is precipitated as hydrochloride by addition of hydrogen chloride 1.40 g, 47%, mp. 280°-282° C.

EXAMPLE 15

6-(3-phtalimidopropyl)-6H-indolo(2,3-b)quinoxaline

Indoloquinoxaline is dissolved in dry dimethylsulfoxide (180 ml) under nitrogen and sodium hydride (1.3 g) is added with good stirring at 35° C. After completed hydrogen gas generation (about 30 minutes) 3-chloro-propylphtalimide (11.20 g) is added in portions at 20° C. After 1 day at this temperature the reaction mixture is poured in water. After filtration, drying, recrystallisation from acetonitrile is carried out 15.10 g, 74%; 74%, mp. 212°-214° C.

EXAMPLE 16

6-(3-aminopropyl)-6H-indolo(2,3-b)quinoxaline. HCl
6-(3-phtalimidopropyl)-6H-indolo(2,3-b)quinoxaline (4.06 g) is heated under reflux (4 hours) in ethanol (200 ml) wherein hydrazine (0.5 ml) has been dissolved. After warm filtration the filtrate is concentrated and dissolved in dry ether and then hydrogen chloride is added. The precipitate formed is sucked and dried, 3.12 g, 57%, mp. 288°-291° C.

EXAMPLE 17

6-(N,N-dimethylaminoethyl)-2,3-dimethyl-6H-indolo(2,3-b)-quinoxaline-phosphonoacetate 6-(N,N-dimethylaminoethyl)-2,3-dimethyl-6H-indolo(2,3-b)quinoxaline (318 mg, 0.001 mole) is dissolved in dioxane-ether (10 ml) and a solution of phosphonoacetic acid (140 mg, 0.001 mole) in dioxan-ether (10 ml) is added. After 2 hours at 25° C. the adduct formed is sucked. Yield 412 mg (90%).

EXAMPLE 18

6-(N,N-dimethylaminoethyl)-2,3-dimethyl-6H-indolo(2,3-b)-quinoxaline-phosphonoformate 6-(N,N-dimethylaminoethyl)-6H-indolo-(2,3-b)quinoxaline . HCl (354.5 mg, 0.001 mole) is dissolved in water (50 ml) wherein acetic acid (2.0 g) and sodium acetate (2.3 g) have been dissolved. To this solution trisodiumphosphonoformate-hexahydrate (300.1 mg, 0.001 mole) in water (15 ml) is added. The solution thus obtained then directly is used for antiviral studies.

TABLE 1

| Compound Example | LD$_{50}$ mouse mg/kg | Herpes Simplex | | μg/ml Raji LD$_{50}$ | μg/ml HeHr LD$_{50}$ |
|---|---|---|---|---|---|
| | | OL$_{50}$ Mouse μg/ml | tissue culture OL$_{50}$ μg/ml | | |
| 4 | >200 | 350 | 1 | 0.9 | 0.7 |
| 5 | 180 | 170 | 1 | 1 | 0.5 |
| 6 | >250 | 3 | <0.5 | 0.9 | 0.7 |
| 8 | >200 | 350 | 1 | 0.9 | 0.7 |
| 9 | >250 | 20 | 1 | 0.8 | 0.7 |
| 10 | 220 | 7 | 0.5 | 1 | 1 |

OL$_{50}$ = concentration for 50% survival

What is claimed is:

1. An indoloquinioxaline of formula I

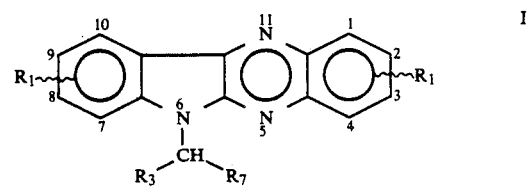

wherein

R$^1$ represents one or more similar or different substituents in the positions 1–4 or 7–10, selected from the group consisting of halogen, lower alkyl or alkoxy group having not more than 4 carbon atoms, trifluoromethyl group and trichloro methyl group;

R$_7$ is a group —(CH$_2$)$_n$—R$_2$ wherein R$_2$ represents NH$_2$, NHR$_4$ or NR$_5$R$_6$ wherein R$_4$, R$_5$ and R$_6$ independently are lower alkyl and n is an integer of from 1 to 4 and R$_3$ represents hydrogen or a lower alkyl or cycloalkyl group having not more than 4 carbon atoms, and physiologically acceptable addition products of the compounds with acids and halogen adducts.

2. An indoloquinoxaline according to claim 1, wherein X is —(CH$_2$)$_n$—R$_2$ wherein R$_2$ is —N(CH$_3$)$_2$ and n is 1.

3. An indoloquinoxalines according to claim 1, characterized in that it is
9-bromo-6-(N,N-dimethylaminoethyl)-6H-indolo(2,3-b)quinoxaline,
2,3-dimethyl-9-bromo-6-(N,N-dimethylaminoethyl)-6H-indolo-(2,3-b)quinoxalin
2,3-dimethyl-6-(N,N-dimethylaminoethyl)-6H-indolo(2,3-b)-quinoxaline,
2-methyl-9-chloro-6-(N,N-dimethylaminoethyl)-6H-indolo(2,3-b)-quinoxaline,
2-methyl-9-bromo-6-(N,N-dimethylaminoethyl)-6H-indolo(2,3-b)-quinoxaline.

4. An indolquinoxalines according to claim 1 characterized in that it is an adduct of an indoloquinoxaline of formula I and a phosphonoalkanoic acid.

5. An indolquinoxalines according to claim 4, wherein the phosphonoalkanoic acid is phosphonoformic acid.

6. An indoloquinoxalines according to claim 4, wherein the phosphonoalkanoic acid is phosphonoacetic acid.

7. An antiviral composition comprising an antivirally effective amount of a substituted indolquinoxaline according to claim I wherein said indolquinoxaline is substituted with phosphonoformic acid, in a pharmaceutically acceptable carrier.

8. An antiviral composition comprising an antivirally effective amount of a substituted indolquinoxaline according to claim 1 wherein said indoloquinoxaline is substituted with phosphonoacetic acid, in a pharmaceutically acceptable carrier.

9. A pharmaceutically acceptable solution having a therapeutic effect against Burkitt lymphoma, osteogenic sarcoma and ascites cancer, comprising a pharmaceutically acceptable carrier and a therapeutically effective concentration of an indoloquinoxaline of formula I

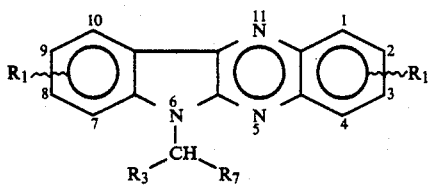

wherein
- $R_1$ represents one or more similar or different substituents in the positions 1–4 or 7–10, selected from the group consisting of lower alkyl or alkoxy group having not more than 4 carbon atoms, trifluoromethyl group and trichloromethyl group;
- $R_7$ is a group —$(CH_2)_n$—$R_2$ wherein $R_2$ represents $NH_2$, $NHR_4$ or $NR_5R_6$ wherein $R_4$, $R_5$ and $R_6$ independently are lower alkyl and n is an integer of from 1 to 4; and
- $R_3$ represents hydrogen or a lower alkyl or cycloalkyl group having not more than 4 carbon atoms, and physiologically acceptable addition products of the compounds with acids and halogen adducts.

10. A method of treating DNA virus infections in a host in need of such treatment which comprises administering an antivirally effective amount of a substituted indoloquinoxaline of formula I

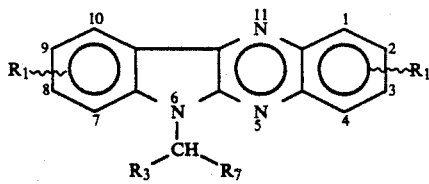

wherein
- $R_1$ represents one or more similar or different substituents in the positions 1–4 or 7–10, selected from the group consisting of halogen, an alkoxy group having not more than 4 carbon atoms, a trifluoromethyl group and a trichloromethyl group;
- $R_7$ is a group —$(CH_2)_n$—$R_2$ wherein $R_2$ represents $NH_2$, $NHR_4$ or $NR_5R_6$ wherein $R_4$, $R_5$ and $R_6$ independently are lower alkyl and n is an interger of from 1 to 4; and $R_3$ represents hydrogen or a lower alkyl or cycloalkyl group having not more than 4 carbon atoms, and physiologically acceptable addition products of the compounds with acids and halogen adducts.

11. A method according to claim 10 wherein said substituted indoloquinoxaline of formula I is an adduct of an indoloquinoxaline of formula I and a phosphonoalkanoic acid.

12. A method for preparing an indoloquinoxaline of formula

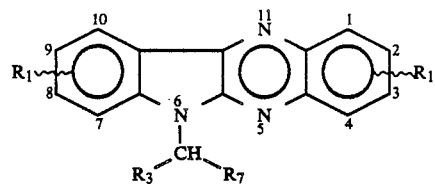

wherein R1 represents one or more similar or different substituents in the positions 1–4 or 7–10, selected from the group consisting of halogen, or alkoxy groups having not more than four carbon atoms, trifluoromethyl, and trichloromethyl; $R_7$ is —$(CH_2)_n$—$R_2$ wherein $R_2$ represents $NH_2$, $NHR_4$, or $NR_5R_6$ wherein $R_4$, $R_5$, and $R_6$ independently are lower alkyl and is an integer of from 1 to 4 and $R_3$ represents hydrogen or a lower alkyl or cycloalkyl group having not more than four carbon atoms, and physiologically acceptable addition of products of the compounds with acids and halogen adducts, comprising the step of:

forming an anionic form of a quinoxaline of formula II:

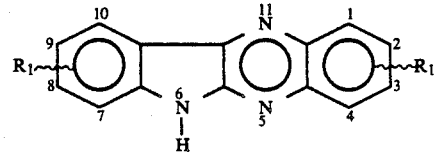

wherein $R_1$ is defined as above;
reacting said anionic form of the quinoxaline with a compound of the formula $ClCHR_3R_7$, wherein $R_3$ and $R_7$ are defined as above; and recovering the compound according to formula I.

13. The method according to claim 12 wherein said quinoxaline is reacted with sodium hydride to obtain the anionic form of said quinoxaline.

* * * * *